United States Patent [19]

Shimada et al.

[11] 4,194,065
[45] Mar. 18, 1980

[54] PROCESS FOR PRODUCING COENZYME Q

[75] Inventors: Yoshio Shimada, Kakogawa; Keiichi Kagotani; Norio Noda, both of Takasago; Hajime Kawaharada, Kakogawa; Kiyoshi Watanabe, Akashi, all of Japan

[73] Assignee: Kanegafuchi Kagaku Kogyo Kabushiki Kaisha, Osaka, Japan

[21] Appl. No.: 843,214

[22] Filed: Oct. 18, 1977

[30] Foreign Application Priority Data

Oct. 26, 1976 [JP] Japan ................................ 51-129106

[51] Int. Cl.² ............................................ C12D 13/02
[52] U.S. Cl. ..................................... 435/133; 435/255; 435/818
[58] Field of Search ........................ 195/82, 28 R, 109

[56] References Cited

U.S. PATENT DOCUMENTS 3,769,170 10/1973 Kondo et al. ........................... 195/82
3,850,753 11/1974 Chibata et al. ....................... 195/109

FOREIGN PATENT DOCUMENTS 673128 of 1972 Japan.

*Primary Examiner*—Alvin E. Tanenholtz
*Attorney, Agent, or Firm*—Armstrong, Nikaido, Marmelstein & Kubovcik

[57] ABSTRACT

A process is disclosed wherein yeast cells containing coenzyme Q in large quantities are efficiently produced by aerobically cultivating a yeast, in which maximum specific growth rate is not less than 0.15 $hr^{-1}$ under optimum cultural conditions, in a nutrient medium in which said yeast can grow, while maintaining the dissolved oxygen concentration in the culture broth at not less than 2 ppm and controlling the average specific growth rate through the whole period of cultivation at not more than 0.1 $hr^{-1}$, and coenzyme Q is recovered from the resulting yeast cells.

12 Claims, No Drawings

PROCESS FOR PRODUCING COENZYME Q

STATEMENT OF THE INVENTION

The present invention relates to a process for the production of coenzyme Q (hereinafter referred to as Co-Q). More specifically, the present invention relates to a process for the advantageous production of Co-Q from yeast cells which are produced efficiently and contain large quantities of Co-Q.

BACKGROUND OF THE INVENTION

Co-Q is a quinone derivative which plays an important role in the terminal electron transport system of organisms. The structure of Co-Q is 2,3-dimethoxy-5-methyl-1,4-benzoquinone having an isoprenoid side chain at the 6 position, and there are various homologs including Co-$Q_6$–Co-$Q_{10}$ depending on the number of the isoprene unit in the side chain. Co-Q occurs in various kinds of organisms and those in yeasts are known to be Co-$Q_6$–Co$Q_{10}$. Their physiological activity and pharmacological effects recently have been elucidated.

Co-Q hitherto has been produced by extraction from animals and plants and partly by chemical synthesis, but the cost is so high that industrial production on a large scale has been difficult. Therefore, attempts to produce Co-Q by fermentation recently have been attempted. However, the Co-Q content of cells produced by the usual method of cultivating microorganisms is rather low. There is a method in which a yeast of the genus Candida is cultivated in a medium containing n-alkane with the addition of a precursor of Co-Q such as p-hydroxybenzoic acid to increase the Co-Q content of cells (Japanese Pat. No. 673,128). However, in this method, the amounts of Co-Q produced per culture broth are small and the carbon source is limited to n-alkane.

In order to carry out the fermentative production of Co-Q, the present inventors extensively examined species of yeast, the composition of media and cultural conditions, and have developed a cultivation method by which yeast cells containing large amounts of Co-Q are produced in high concentrations.

The production of Co-Q with use of microorganisms must be considered with respect to both the Co-Q content of cells and the cell productivity from the point of view of the production cost. So far, in the production of Co-Q using yeast, the cultivation method which attached importance to an increase in the Co-Q content sacrificed the productivity of cells whereas, on the other hand, the employment of the usual method for efficiently producing cells resulted in a decrease in the Co-Q content of cells.

The present inventors considered that the maintenance of highly oxidative conditions during cultivation would exert a favorable influence on the formation of Co-Q in view of the important role of Co-Q in oxidative reactions in organisms. In order to maintain the oxidative state of the environment in which cells grow, the concentration of dissolved oxygen in a culture medium must be raised. An increase in the oxygen supply or a decrease in the oxygen consumption will lead to an increase in dissolved oxygen in a culture medium. The present inventors investigated the relationship between the concentration of dissolved oxygen in a culture medium (hereinafter referred to as D.O.) and both the Co-Q content of cells and the cell productivity with various yeasts, and have found that yeast cells produced under conditions of high D.O. contain large amounts of Co-Q.

Many methods for the efficient production of yeast cells are known, for example, one in which aeration and agitation are increased in order to raise the rate of oxygen supply; one in which the partial pressure of oxygen in aerating gases is increased; one in which cultivation is carried out under elevated pressures; and one in which the cultivation apparatus is improved. However, an increase in oxygen supply to the culture broth in the usual cultivation processes for the production of cell mass leads to an increase in cell productivity (hereinafter referred to as $\mu x$: g. cells produced/l/hr) and an increase in the oxygen consumption proportional to the increase in $\mu x$ and, as a result, owing to decreased D.O., it is difficult to keep the oxidative environment suitable for the formation of Co-Q. The Co-Q content of yeast cells grown under conditions of maintaining D.O. values at not less than 2 ppm by supplying sufficient amounts of oxygen for the growth of cells in disregard of the production cost is sometimes higher than that of yeast cells cultivated at D.O. of not more than 1 ppm. But an increase in D.O. does not necessarily raise the Co-Q content of yeast cells, depending on kinds of yeasts, cultural conditions (temperature and pH) and the composition of media.

Cultivating yeast while regulating D.O. at not less than 2 ppm and changing cultural conditions and the composition of media, the present inventors investigated the relation of the Co-Q content of cells to the cell concentration (hereinafter referred to as X), the specific growth rate (hereinafter referred to as $\mu$) and cell productivity ($\mu x$) at each cultivation time, and have found that there is a clear correlation between the Co-Q content of cells and $\mu$. The Co-Q content of cells tends to increase when a yeast which exhibits a maximum specific growth rate of not less than 0.15 hr$^{-1}$ under the optimum cultural condition is cultivated while the average specific growth rate ($\mu$ from the beginning to the end of cultivation) is controlled by means of cultural conditions and the composition of media. Especially when the yeast is cultivated at the average specific growth rate of not more than 0.1 hr$^{-1}$, the Co-Q content of cells is markedly increased.

The optimum cultural conditions somewhat vary according to the kinds of yeasts, but generally are presented as follows:
Cultivating Apparatus: jar fermentor;
Medium: glucose 20 g/l, peptone 10 g/l, and yeast extract 5 g/l;
Temperature: 25°–35° C.
Agitation: 700 rpm;
Aeration: 2 vvm.

The present inventors have further examined in detail the relation of the Co-Q content to D.O., $\mu, \mu x$, and methods for regulating $\mu$, and have succeeded in developing a cultivation method favorable for the Co-Q production. The present inventors have found that yeast cells containing Co-Q in large quantities are efficiently produced by maintaining the average specific growth rate of not more than 0.1 hr$^{-1}$ and D.O. of not less than 2 ppm, and completed the present invention based on this finding.

DETAILED DESCRIPTION OF THE INVENTION

The present invention is a process for advantageous production of Co-Q wherein a yeast, in which the maximum specific growth rate is not less than 0.15 hr$^{-1}$ under optimum cultural condition, is cultivated in a nutrient medium in which said yeast can grow while the dissolved oxygen concentration in the culture broth is maintained at not less than 2 ppm and the average specific growth rate through the whole period of cultivation is controlled at not more than 0.1 hr$^{-1}$, and Co-Q is recovered from the resulting yeast cells.

The process of the present invention is applicable irrespective of the kinds of Co-Q homologs (Co-Q$_6$–Co-Q$_{10}$) contained in the yeast cells.

For the efficient production of yeast cells such as SCP (single cell protein), D.O. usually is controlled at about 0.5 ppm, because oxygen is not a rate-determining factor for $\mu$X at D.O. of more than 0.5 ppm. The culturing method of the present invention wherein $\mu$ is regulated while D.O. is maintained at high concentrations of not less than 2 ppm can be regarded as a new characteristic method for producing Co-Q.

In cultivation of yeast cells in a standard fermentation vessel under depressed $\mu$, the Co-Q content of cells increases, but an increase in productivity of Co-Q is not so high because of low $\mu$X. The culturing method of the present invention is an advantageous one for Co-Q production by fermentation designed to remedy the drawbacks of conventional methods. In this process, both usual and specially-devised fermentation vessels can be used.

By regulating $\mu$ and D.O. during cultivation, cells containing large amounts of Co-Q can be efficiently and constantly produced.

Although depressing $\mu$ sometimes causes a decrease in $\mu$X, it is possible to produce cells high in Co-Q without a decrease in $\mu$X by cultivation in high concentrations (either batchwise or continuous cultivation) in which a decrease in $\mu$ is offset by an increase in X.

Aeration with oxygen gas and cultivation under elevated pressure, which are generally not employed on account of their high costs, can be employed as a useful method in the present invention.

A yeast which can be employed in the present invention may be any type of yeast which contains Co-Q and in which maximum specific growth rate is not less than 0.15 hr$^{-1}$ under optimum cultural condition. Especially a yeast which belongs to the genus Rhodotorula, Cryptococcus, Candida, Trichosporon or Torulopsis can advantageously be employed. As strains, for example, *Rhodotorula mucilaginosa* AHU 3946, *Cryptococcus albidus* AHU 3922, *Candida utilis* IAM 4200, *Trichosporon fermentans* ATCC 10675 and *Torulopsis magnoliae* IFO 0705 can be employed.

In the process of the present invention, oridinary nutrient media can be used. Any carbon source which can be assimilated by the yeast to be employed may be used. Examples of the carbon sources include sugars such as glucose, sucrose, fructose, starch hydrolysate, molasses, sulfite waste liquor, or liquor resulting from wood saccharification; organic acids such as acetic acid, fumaric acid, citric acid, maleic acid or lactic acid; alcohols such as methanol, ethanol or propanol; and further include liquid hydrocarbons, fats and oils, glycerol, whey and agricultural wastes which can be utilized by the yeast to be employed. Inorganic or organic compounds such as ammonium sulfate, ammonium chloride, ammonium phosphate, ammonia water, urea, amino acids, peptone, and hydrolysate of soy bean protein are used as nitrogen sources. As minerals, salts of potassium, magnesium, phosphoric acid, zinc, iron, manganese, copper and calcium can be used. If necessary, other minor metal salts, yeast extract, meat extract, corn steep liquor, vitamins and nucleic acid-related compounds may be added to the media.

Cultivation is carried out aerobically in a batchwise or continuous manner at any pH and temperature which allows the yeast to grow; that is, at pH 2–8 and a temperature of 20°–45° C. Oxygen is supplied by aeration with air, oxygen gas or their mixtures. The generally used cultivation apparatus, such as those of aeration-agitation or air-lift type or specially devised types, can be employed as the cultivation apparatus.

For controlling D.O. level during cultivation, aerating methods such as change in partial pressure of oxygen by aerating air, oxygen or mixtures thereof, change in contact area or contact time between aerated gases and culture liquid, cultivation under elevated pressures or combinations of the above-mentioned methods can be employed.

Specific growth rate ($\mu$) is calculated according to the following formula by determining the cell concentrations at each cultivation time.

In batchwise cultivation:

$$\mu = \frac{\log_{10}\left(\frac{X_t}{X_o}\right) \times 2.302}{t}$$

$X_o$ = initial cell concentration;
$X_t$ = cell concentration time after t hours; and
t = cultivation time, hr.

In continuous cultivation:

$$\mu = \frac{\text{cell mass in overflow during } t_c \text{ hours}}{\text{cell mass in a vessel} \times t_c}$$

$t_c$ = period of continuous culture (hr)

Average specific growth rate is defined as the $\mu$ value which is calculated from the beginning to the end of cultivation in the case of batchwise culture, or the $\mu$ value which is calculated from the beginning to the end of continuous cultivation in the case of continuous culture.

For controlling $\mu$, any method, the condition of which does not inhibit the formation of Co-Q and yet falls within the limits for the growth of yeast cells, can be employed. For example, the control of cultural conditions such as temperature and pH, that of the addition amount of carbon, nitrogen and mineral sources, and that of the amount of growth factors such as vitamins, amino acids and nucleic acid-related compounds can be carried out as a means of controlling $\mu$. Further, for controlling $\mu$, chemicals which depress the growth of cells and yet do not inhibit the formation of Co-Q, for example, organic acids such as formic acid, acetic acid, propionic acid, caprylic acid, pelargonic acid, capric acid, citric acid, malonic acid, succinic acid, fumaric acid, and salts thereof, and alcohols such as methanol, ethanol, propanol, amyl alcohol and octyl alcohol may be added. The methods for controlling $\mu$ described above, that is, the control of cultivation temperature, pH and the composition of media, and the addition of growth-inhibiting chemicals can be employed independently or in combinations. The choice of methods for controlling $\mu$ depends on the kinds of yeasts, carbon sources, etc., but the control by temperature and pH are preferable. The control of $\mu$ may be performed at any time of cultivation and for any length of the period. During cultivation, $\mu$ can be varied to any value, but the control of $\mu$ at not more than 0.1 hr$^{-1}$ gives a good result. In any case, the average specific growth rate through the whole period of cultivation must be not more than 0.1 hr$^{-1}$.

The final cell concentration may be any value but the cultivation in high cell concentrations of not less than 20 g, drycell/l is preferable because of an increase in $\mu X$.

The Co-Q content of yeast cells thus obtained is high and the cost for extraction and purification per unit weight of Co-Q is much reduced.

For the isolation of Co-Q from yeast cells produced by the process of the present invention, conventional methods can be employed. For example, yeast cells are saponified with a methanolic alkali in the presence of pyrogallol and extracted with organic solvents such as petroleum ether, chloroform, etc. Further purification is carried out by means of adsorption chromatography on alumina, silica gel, florisil, etc. and pure crystals can be obtained by recrystallization. The crystals thus obtained perfectly coincide with Co-Q produced by the conventional cultivation method in respect of physical and chemical properties, such as melting point, UV spectra, IR spectra and mass spectra.

The following examples will illustrate the present invention in greater detail.

EXAMPLE 1

*Rhodotorule mucilaginosa* AHU 3946 was cultivated in a 20 l medium containing $KH_2PO_4$ 4 g/l, $(NH_4)_2SO_4$ 1 g/l, $MgSO_4.7H_2O$ 1 g/l, $ZnSO_4.7H_2O$ 10 mg/l, $FeSO_4.7H_2O$ 100 mg/l, yeast extract 1 g/l, ethanol 2 g/l, at 30° C., pH 5.0, agitation 1000 rpm and aeration 1 vvm (aeration with air is the standard condition) in a jar fermentor until the cell concentration reached 20 g (dry wt.)/l.

During cultivation, the pH was adjusted with ammonia water, and the concentration of ethanol was kept at not less than 1 g/l by feeding. The concentration of D.O. was measured with a Beckman D.O. meter and controlled to a constant level by aerating a mixture of air, oxygen gas and nitrogen gas in an appropriate ratio. Specific growth rate ($\mu$) was estimated by measuring cell concentration at each cultivation time (hr), and controlled by varying temperature in a range of 23°–33° C. and pH in a range of 3–5 so that the average $\mu$ during the whole cultivation period might approach the desired value. The relationship between D.O., the average specific growth rate and the Co-Q content is shown in Table 1.

TABLE I

| Average D.O. $\mu(hr^{-1})$ (ppm) | Co-Q content of cells (mg/g) | | | | |
|---|---|---|---|---|---|
| | Not Controlled* | 0–1 | 1–2 | 2–4 | 4–7 |
| 0.13–0.18 | 0.30 | 0.25 | 0.28 | 0.38 | 0.35 |
| 0.08–0.10 | — | 0.31 | 0.40 | 0.91 | 0.85 |
| 0.04–0.07 | — | 0.41 | 0.45 | 1.15 | 1.28 |

*Cultivated under standard conditions, D.O. was 7–9 ppm at the beginning and 0–1.5 ppm at the end.

Yields of Co-Q formed based on ethanol consumed (YCo-Q), amounts of Co-Q produced per liter of the culture broth and amounts of crystals obtained from cells are shown in Table 2.

TABLE 2

| D.O. (ppm) | $\mu$ (hr$^{-1}$) | YCo-Q (mg/g) | Co-Q formed (mg/l) | Yield of crystals (mg/l) |
|---|---|---|---|---|
| Not controlled | 0.17 | 0.17 | 6.0 | 3.7 |
| 0–1 | 0.15 | 0.13 | 5.0 | 3.0 |
| 2–4 | 0.10 | 0.41 | 18.2 | 11.5 |
| 4–7 | 0.06 | 0.51 | 25.6 | 14.7 |

The crystals were confirmed to be Co-Q$_{10}$ from melting point, UV spectrum, mass spectrum and paper chromatograph.

EXAMPLE 2

*Cryptococcus albidus* AHU 3922 was cultivated in a 20 l medium containing palmitic acid 30 g/l, $KH_2PO_4$ 4 g/l, $(NH_4)_2SO_4$ 1 g/l, $MgSO_4.7H_2O$ 2 g/l, $ZnSO_4.7H_2O$ 10 mg/l, $FeSO_4.7H_2O$ 100 mg/l, and corn steep liquor 2 g/l, (pH was adjusted to 5) in the same manner as in Example 1. Table 3 shows D.O., the average $\mu$, and the Co-Q content of cells. Yield for extraction and purification of Co-Q was 0.57–0.62. The crystals thus obtained were confirmed to be Co-Q$_{10}$.

TABLE 3

| Average D.O. $\mu(hr^{-1})$ ppm | Co-Q content of cells (mg/g) | | | | |
|---|---|---|---|---|---|
| | Not controlled* | 0–1 | 1–2 | 2–4 | 4–7 |
| 0.1–0.15 | 0.15 | 0.18 | 0.21 | 0.25 | 0.20 |
| 0.07–0.09 | — | 0.23 | 0.32 | 0.55 | 0.61 |
| 0.03–0.05 | — | 0.25 | 0.30 | 0.73 | 0.66 |

*Cultivated under standard conditions, D.O. was 7–9 ppm at the beginning and 0–1 ppm at the end.

EXAMPLE 3

*Candida utilis* IAM 4200 was cultivated by a continuous culture method in a 10 l medium containing $H_3PO_4$ 3 g/l, KCl 2 g/l, $MgSO_4.7H_2O$ 2 g/l, $(NH_4)_2SO_4$ 2 g/l, $ZnSO_4.7H_2O$ 30 mg/l, $FeSO_4.7H_2O$ 100 mg/l, corn steep liquor 2 g/l, thiamine hydrochloride 1 mg/l, and acetic acid 3 g/l (pH was adjusted to 6.5 with ammonia water) at 33° C., pH 6.5, agitation 700 rpm and aeration 1 vvm (aeration with air is the standard condition). The pH during cultivation was adjusted with $H_2SO_4$ or NaOH and $CH_3COONH_4$ was fed so as to keep the concentration of 1–3 g/l as a free acid. The D.O. during cultivation was controlled in the same manner as in Example 1. The $\mu$ was controlled in the same manner as in Example 1 in pre-culture, and in the continuous culture $\mu$ was estimated from the necessary volume of the culture broth withdrawn from the vessel for maintaining the steady state of the cell concentration in the culture broth and controlled by varying cultivation temperature in a range of 25°–35° C., and pH in a range of 5–7. The results of the continuous culture for 96 hr. are shown in Table 4. Cell yields based on acetic acid consumed were 0.35–0.41 in each case. Yields of Co-Q crystals obtained from cells were 0.61–0.70. The crystals were confirmed to be Co-Q$_7$.

TABLE 4

| D.O. (ppm) | Average $\mu(hr^{-1})$ | Cell concentration (%) | Co-Q content (mg/g) | Cell productivity (g/l/hr) | Cell productivity (mg/l/hr) |
| --- | --- | --- | --- | --- | --- |
| Not controlled* | 0.25 | 1.7 | 0.37 | 4.3 | 1.6 |
| 0–1 | 0.08 | 3.5 | 0.52 | 2.8 | 1.5 |
| 0–2 | 0.10 | 4.8 | 0.60 | 4.8 | 2.9 |
| 2–4 | 0.22 | 3.2 | 0.31 | 7.0 | 2.2 |
| 2–4 | 0.09 | 4.5 | 1.05 | 4.1 | 4.3 |
| 2–4 | 0.05 | 6.5 | 1.21 | 3.3 | 4.0 |

*Cultivated under standard conditions

EXAMPLE 4

*Torulopsis magnoliae* IFO 0705 or *Trichosporon fermentans* ATCC 10657 was cultivated in a 10 l medium containing $KH_2PO_4$ 4 g/l, $(NH_4)_2SO_4$ 3 g/l, $MgSO_4\cdot 7H_2O$ 2 g/l, $ZnSO_4\cdot 7H_2O$ 20 mg/l, $FeSO_4\cdot 7H_2O$ 50 mg/l, yeast extract 1 g/l, corn steep liquor 1 g/l (pH was adjusted to 5) and glucose or glycerol as a carbon source, at 33° C., pH 2–6, agitation 500 rpm, aeration 0.1–2.0 vvm (pH 5, 1 vvm of aeration with air is the standard condition), until the cell concentration reached 30 g/l. A carbon source was fed intermittently in an amount of 10 g/l each, so as not to starve cells. The control of D.O. was conducted according to the method described in Example 1. The specific growth rate was regulated by adding a growth-inhibiting agent and varying pH, D.O., the average growth rate and the Co-Q content are shown in Table 5. The crystals of Co-Q isolated from cells were Co-$Q_9$.

TABLE 5

| | | Co-Q content of cells (mg/g) | | | |
| --- | --- | --- | --- | --- | --- |
| Strain Carbon Source | | Torulopsis magnoliae Glucose | | Trichosporon fermentans Glycerol | |
| growth inhibiting agent | average $\mu(hr^{-1})$ D.O. (ppm) | Not[1]* controlled | 2–4 | Not[1]* controlled | 2–4 |
| none | 0.15–0.31 | 0.43 | 0.40 | 0.38 | 0.50 |
| | 0.04–0.10 | 0.58 | 1.05 | 0.41 | 0.95 |
| methanol* 0.5–1.0% | 0.13–0.20 | 0.39 | 0.55 | 0.43 | 0.73 |
| | 0.05–0.09 | 0.60 | 1.21 | 0.40 | 1.15 |
| caprylic acid 0.5g/l | 0.12–0.18 | 0.42 | 0.51 | 0.32 | 0.41 |
| | 0.03–0.07 | 0.55 | 1.08 | 0.41 | 1.30 |
| formic*[2] acid 1–2g/l | 0.15–0.25 | 0.33 | 0.61 | 0.41 | 0.38 |
| | 0.06–0.10 | 0.33 | 1.35 | 0.50 | 1.25 |

*[1] Cultivated under standard conditions, D.O. was 8–10 ppm at the beginning and 0–1 ppm at the end.
*[2] Concentration was kept by supplement.

What is claimed is:

1. A process for producing coenzyme Q which comprises aerobically cultivating a yeast in a fermentor, in which maximum specific growth rate is not less than 0.15 hr$^{-1}$ under optimun cultural conditions, in a nutrient medium containing a carbon source in which said yeast can grow, while maintaining the dissolved oxygen concentration in the culture broth at not less than 2 ppm and controlling the average specific growth rate through the whole period of cultivation at not more than 0.1 hr$^{-1}$, and recovering coenzyme Q from the resulting yeast cells.

2. The process according to claim 1 wherein said yeast belongs to a genus selected from the group consisting of Rhodotorula, Cryptocuccus, Candida, Trichosporon, and Torulopsis.

3. The process according to claim 1 wherein the carbon source used in the nutrient medium is a member selected from the group consisting of sugars, organic acids, alcohols, liquid hydrocarbons, fats and oils, glycerol, whey and agricultural wastes.

4. The process according to claim 1 wherein the aerobic cultivation is carried out by aeration with a member selected from the group consisting of air, oxygen gas and mixtures thereof.

5. The process according to claim 1 wherein the fermentor to be used is an aeration-agitation type or an air-lift type fermentor.

6. The process according to claim 1 wherein the specific growth rate of the yeast is controlled by cultivation in high concentrations.

7. The process according to claim 1 wherein the specific growth rate of the yeast is controlled by control of cultivation temperature.

8. The process according to claim 1 wherein the specific growth rate of the yeast is controlled by adding a member selected from the group consisting of organic acids, salts thereof and alcohols.

9. The process according to claim 1 wherein the cultivation is carried out either batch-wise or continuously.

10. The process according to claim 1 wherein the recovered coenzyme Q is coenzyme $Q_6$–$Q_{10}$.

11. The process according to claim 1 wherein the specific growth rate of the yeast is controlled by the pH of the medium.

12. The process according to claim 1 wherein the specific growth rate of the yeast is controlled by the amount of minerals present in the medium.

* * * * *